Figure 1:
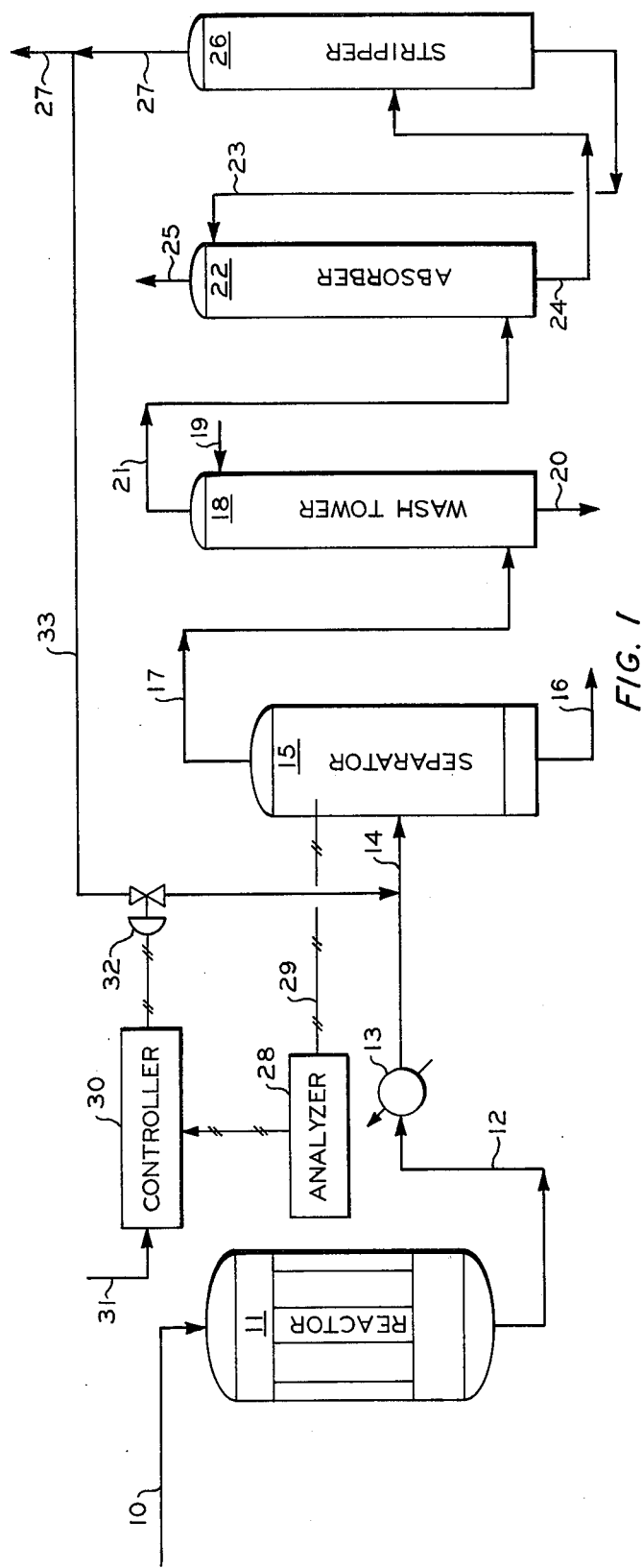

United States Patent [19] [11] 4,069,272
Hutson, Jr. [45] Jan. 17, 1978

[54] OXIDATIVE DEHYDROGENATION EFFLUENT CONTROL

[75] Inventor: Thomas Hutson, Jr., Bartlesville, Okla.

[73] Assignee: Phillips Petroleum Company, Bartlesville, Okla.

[21] Appl. No.: 661,456

[22] Filed: Feb. 25, 1976

[51] Int. Cl.² .............................................. C07C 11/12
[52] U.S. Cl. ................................................. 260/680 E
[58] Field of Search ............. 260/680 E, 680 D, 683.3

[56] References Cited

U.S. PATENT DOCUMENTS

| | | | |
|---|---|---|---|
| 2,384,645 | 9/1945 | Schulze | 260/680 R |
| 2,991,321 | 7/1961 | Voge et al. | 260/680 E |
| 3,168,587 | 2/1965 | Michaels et al. | 260/683.3 |
| 3,518,284 | 2/1967 | Foster | 260/680 E |
| 3,709,951 | 1/1973 | Hutson | 260/680 E |
| 3,721,253 | 3/1973 | Remke | 137/3 |
| 3,728,413 | 4/1973 | Woerner | 260/680 E |

Primary Examiner—Delbert E. Gantz
Assistant Examiner—Joseph A. Boska

[57] ABSTRACT

Organic compounds, especially hydrocarbons, are oxidatively dehydrogenated by contacting them with an oxygen-containing gas and steam under dehydrogenation conditions, and, following this reaction, the oxygen concentration in the organic portion of the effluent stream is maintained below the combustible limit by the addition of a stream recycled from a downstream purification step responsive to measurement of the oxygen concentration in the organic effluent stream from which the bulk of the water vapor has been removed. In one embodiment, hydrocarbons are oxidatively dehydrogenated by contacting with steam and an oxygen-containing gas over a catalyst, following which water is condensed from the effluent and it is diluted with a recycled diolefin concentrate stream responsive to the oxygen concentration in the gas phase of the effluent separation vessel so as to regulate the residual oxygen concentration in the hydrocarbon portion of the effluent to a safe value below 9.5 mole percent.

7 Claims, 2 Drawing Figures

OXIDATIVE DEHYDROGENATION EFFLUENT CONTROL

This invention relates to oxidative dehydrogenation. In another aspect, this invention relates to controlling the oxygen concentration in the organic effluent from an oxidative dehydrogenation process below the combustible limit by the addition of a recycled product stream. In accordance with still another aspect, this invention relates to controlling the oxygen concentration in an olefin oxidative dehydrogenation process effluent stream, following removal of the major portion of the water therefrom, by addition of a plant hydrocarbon stream comprising butadiene and butenes responsive to a measured oxygen concentration. In a further aspect, this invention relates to the oxidative dehydrogenation of hydrocarbons and the control of the residual oxygen concentration in the hydrocarbon portion of the oxidative dehydrogenation effluent at a desired value below the combustible limit, by dilution with a plant hydrocarbon stream.

In chemical reactions of various organic materials where oxygen is present, it is common practice to employ a moderate excess of oxygen-containing gas during the reaction in order to achieve the desired level of conversion of the feed components. In partial-conversion processes, the presence of surviving oxygen, not consumed during the oxidation reaction, in the organic-diluent mixture leads to operational hazards due to the oxygen becoming progressively more concentrated in process effluent streams whereby the combustible limit may be exceeded. One commercial process in which non-reacted oxygen in the effluent is a problem is the oxidative dehydrogenation of hydrocarbons. The present invention is directed to controlling the oxygen concentration in effluents from this and other oxidation processes so as to maintain or regulate the oxygen concentration below the combustible or explosive limit at critical process locations.

Accordingly, an object of this invention is to provide an improved process for the treatment of effluents from oxidation processes.

Another object of this invention is to provide an improved process for the oxidative dehydrogenation of hydrocarbons.

Another object of this invention is to provide a method for controlling the concentration of oxygen in organic-containing effluents from oxidation processes.

A further object of the invention is to provide a method for maintaining the oxygen concentration in process effluents below the combustible limit.

Figure 2:
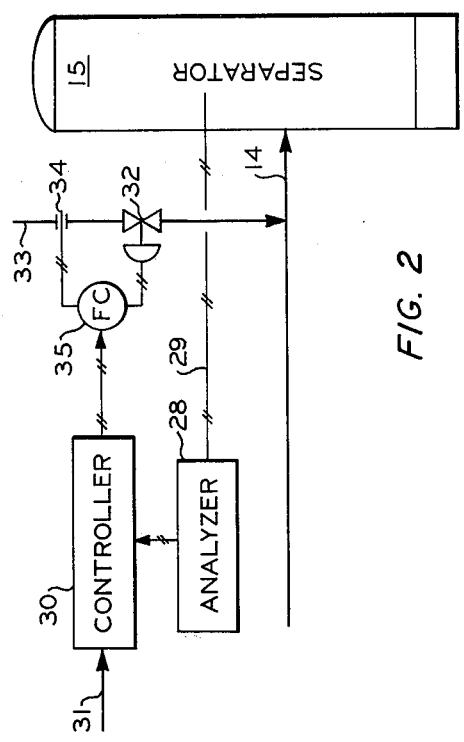

Other objects, aspects, and the several advantages of the invention will be apparent to those skilled in the art upon a study of the disclosure, the accompanying drawings, FIGS. 1 and 2, and the appended claims.

In accordance with the invention, a process is provided for controlling and regulating the oxygen concentration in an oxidative dehydrogenation process hydrocarbon stream effluent following diluent removal to a level below the combustible limit by dilution of the effluent with a recycled hydrocarbon stream responsive to a measured oxygen concentration in the effluent stream.

In accordance with one specific embodiment, the oxygen concentration in the effluent from an oxidative dehydrogenation process for the conversion of hydrocarbons to more unsaturated hydrocarbons is maintained below the combustible limit by the addition of a plant hydrocarbon stream such as a butadiene-butenes mixture responsive to a measured oxygen concentration in the effluent.

In accordance with another embodiment, the oxygen concentration in the effluent stream from a butenes oxidative dehydrogenation reaction, after condensation of steam therefrom, is maintained below the combustible limit by the addition of a recycle plant hydrocarbon stream, such as butadiene-butenes, by measuring the oxygen concentration in the effluent and manipulating the flow of the added plant hydrocarbon stream to maintain an oxygen concentration of 9.5 mole percent or less, preferably 7.5 mole percent or less.

As indicated above, the instant invention is applicable to any process in which the oxygen concentration in a plant stream may be equal to or greater than the combustible limit at critical locations due to the nature of the separations processes. The invention is particularly applicable to maintaining the oxygen concentration below the combustible limit in the effluent from a hydrocarbon oxidative dehydrogenation process such as disclosed in U.S. Pat. Nos. 3,725,493 and 3,709,951. Both of these patents are hereby incorporated by reference. The reactants, catalysts, and conditions normally employed for the oxidative dehydrogenation processes are set forth in said patents.

A better understanding of the invention will be obtained upon reference to the accompanying drawings in which FIG. 1 illustrates an embodiment thereof wherein the oxygen concentration in the effluent from a butene oxidative dehydrogenation process is controlled at a level below the combustible limit, and in which FIG. 2 illustrates a preferred control system.

Referring now to FIG. 1, feed hydrocarbon comprising butenes and some butane together with steam and oxygen-enriched air are introduced into reactor 11 by way of line 10. Reactor 11 can contain a catalyst employed at hydrocarbon/oxygen/steam ratios and operating conditions such as disclosed in U.S. Pat. No. 3,725,493. In the present embodiment, reactor 11 is operated at an inlet temperature of about 500° C and an outlet temperature of about 590° C at an average pressure of about 2.7 Kg/cm$^2$.

Oxidative dehydrogenation effluent is removed from reactor 11 by way of line 12 and is passed through cooler 13. This effluent stream comprises butadiene, unconverted butenes, butane, oxygen, nitrogen, a considerable concentration of steam, and traces of oxygenated hydrocarbons and carbon oxides. The effluent stream is cooled in heat exchanger 13 sufficiently to condense the bulk of the steam present in the effluent stream such as to 49° C. The cooled effluent stream which now contains water condensate is passed by line 14 to separator vessel 15 operated at a pressure of about 2.1 Kg/cm$^2$ wherein water condensate is removed as bottoms by way of line 16. The water condensate removed from the bottom of separator vessel 15 by way of line 16 can also contain oxygenated hydrocarbons, such as carbonyls, and other soluble and/or condensible impurities. The remainder of the dehydrogenation effluent is removed overhead from separator 15 by way of line 17, and this stream comprises butadiene, unconverted butene, butane, nitrogen, oxygen, and minor concentrations of other materials.

The butadiene-butenes-containing stream 17 is passed to wash tower 18 wherein the stream is contacted with a wash liquid such as water introduced by line 19 and which is removed along with materials such as additional oxygenated hydrocarbons washed from the effluent as bottoms by way of line 20 for recovery or disposal as desired. A hydrocarbon-containing stream comprising butadiene, butenes, nitrogen, and oxygen and other gases is removed overhead from wash tower 18 by way of line 21 and passes to absorber 22.

In absorber 22 the effluent stream is countercurrently contacted by an oil absorption medium introduced at the upper portion of absorber 22 by way of line 23 which medium absorbs butadiene, butenes, and any other $C_4$ and heavier hydrocarbons present which are removed along with the rich absorption medium from the bottom of absorber 22 by way of line 24. The nitrogen, oxygen, and other light gases contained in washed gas stream 21 are rejected as the overhead gas stream 25 from oil absorber 22. The bottoms stream 24 is passed to stripper 26 wherein butadiene, butenes, and residual butane are heat stripped and removed overhead by line 27. Stripped absorption medium is removed from the bottom of vessel 26 and returned to absorber 22 by line 23. The butadiene-butenes-containing stream removed overhead from stripper 26 is passed by way of line 27 to further separation and purification of the contained butadiene or to other use. A portion of this stream is recycled by line 33 as described below.

In accordance with the invention, the oxygen concentration in the gas phase of separator 15 is determined by analyzer 28 such as a gas chromatographic analyzer, receiving the separator gas sample via line 29. A signal responsive to this analysis is transmitted to analysis controller 30 wherein this vaue is compared with a desired set point value of oxygen concentration, such as a value between 5.0 and 9.5 mole percent, for example, 7.2 mole percent, applied as signal 31. Responsive to the difference between these two values, controller 30 generates an output signal, in conventional manner, which is applied to control valve 32. Valve 32 controls the rate of addition of the recycled butadiene-butenes stream through line 33 for introduction into line 14 closely downstream of condenser 13 to increase the hydrocarbon concentration in the dehydrogenation effluent so that the oxygen cncentration in the effluent is diluted and maintained concentration below the combustible limit which is approximately 9.5 mole present oxygen.

In accordance with a preferred embodiment of this invention, a cascade control system is provided in FIG. 2 wherein the control signal from analysis controller 30 is applied as the set point to the butadiene-butenes stream 33 flow control loop comprised of flow measuring element 34, flow controller 35, and valve 32.

As can be seen from the description of the above drawing, the oxygen concentration in vessel 15 and in effluent line 17 from the oxidative dehydrogenation process after condensation of steam therefrom by heat exchanger 13 is maintained below the combustible limit of about 9.5 mole percent oxygen by introduction of a portion of the separation butadiene-butenes stream removed in line 27. The flow rate of butadiene concentrate recycled by way of line 33 into effluent line 14 is controlled responsive to the oxygen concentration in the gas phase of separator 15. Responsive to this measurement, the rate of flow of butadiene concentrate recycled through line 33 is manipulated by valve 32 to maintain the oxygen concentration safely below 9.5 mole percent such as at 7.2 mole percent (7.5 mole percent dry basis). The use of a butadiene concentrate stream as the hydrocarbon diluting medium for regulating the oxygen concentration in the effluent stream results in more efficient downstream separation, e.g., in vessels 18, 22, and 26, than could be obtained, say, if inert diluents such as nitrogen or $CO_2$ were introduced into the effluent stream to maintain the oxygen concentration at a desired level. The use of nitrogen or carbon dioxide would seriously overload absorber 22 in particular, as well as being costly to obtain and compress for such use.

SPECIFIC EXAMPLE

The following calculated specific example illustrates the effectiveness of the inventive method of controlling the oxygen concentration in the effluent from a butene oxidative dehydrogenation reactor below the combustible limit. Feed stream 10 comprises 27.4 Kg/Hr of hydrocarbon and 33.2 Kg/Hr of enriched air (36.5 mole percent oxygen) diluted by 299.4 Kg/Hr of superheated steam. Following the oxidative dehydrogenation reaction and the condensation of the bulk of the steam and the additional water vapor formed by oxidation of the liberated hydrogen, 17.6 Kg/Hr of butadiene concentrate are added from line 33 to line 14 whereby the vapor portion of this stream and the vapor flowing through separator 15, line 17, wash tower 18 and line 21 contains about 7.2 mole percent oxygen on a water-vapor-saturated basis at about 49° C.

Without the addition of the butadiene concentrate stream, the oxygen concentration in the cooled effluent vapor (lines 14 and 17) would be about 11.9 percent as shown by the following table of compositions and would present a severe explosion hazard if a source of ignition were encountered.

TABLE I

| Component | Feed $10^a$ | Effluent $17^c$ | Butadiene Concentrate 27 | Effluent 17 with Recycle$^d$ |
|---|---|---|---|---|
| $C_4H_6$ | 1.2 | 22.8 | 69.7 | 40.1 |
| $C_4H_8$-1 | 1.1 | 0.8 | 2.3 | 1.3 |
| $C_4H_8$-2 | 28.1 | 8.0 | 24.5 | 14.1 |
| $C_4H_{10}$ | 1.0 | 0.9 | 3.5 | 2.0 |
| $O_2$ | 25.0 | 11.9 | — | 7.2 (Set point)$^e$ |
| $N_2$ | 43.5 | 48.5 | — | 29.4 |
| Misc.$^b$ | 0.1 | 3.1 | 0.0 | 1.9 |
| $H_2O$ | dry basis | 4.0 | — | 4.0 |

TABLE I-continued

| | Mol Percent | | | |
|---|---|---|---|---|
| Component | Feed 10[a] | Effluent 17[c] | Butadiene Concentrate 27 | Effluent 17 with Recycle[d] |
| | 100.0 | 100.0 | 100.0 | 100.0 |

[a]Air and butenes calculated together; actual addition of butenes to air (enriched to 36.5 mole percent oxygen) takes place in presence of steam feed as in U.S. Pat. No. 3,709,951, thereby the mixture is noncumbustible.
[b]Includes $C_3$ and lighter hydrocarbons and carbon oxides.
[c]Without butadiene concentrate recycle, normalized to include 4.0 percent water vapor at knock-out tank 15 conditions (wet basis).
[d]With butadiene concentrate recycle in weight ratio of 1/0.643, normalized to include 4.0 percent water vapor at knock-out tank 15 conditions.
[e]Set point for controller 30 (7.5 mole percent oxygen on dry basis).

I claim:

1. In a process for oxidatively dehydrogenating olefins in the presence of an oxygen-containing gas to produce an effluent containing the corresponding diolefin, unconverted olefins, steam, and oxygen, and cooling of the effluent sufficiently to condense steam leaving a gaseous effluent containing diolefin, unconverted olefins, and oxygen, the improvement for controlling the oxygen concentration below the combustible limit in said gaseous effluent which comprises:
   a. measuring the oxygen concentration of said gaseous effluent and producing a signal representative of said concentration, and
   b. controlling said oxygen concentration in said effluent responsive to said signal by diluting same with a recycled $C_4$ hydrocarbon-containing stream introduced into said cooled effluent at a rate sufficient to regulate the residual oxygen concentration in said gaseous effluent to a safe value below 9.5 mole percent.

2. A process according to claim 1 wherein said gaseous effluent is diluted with a butadiene-butenes recycle stream in an amount sufficient to maintain an oxygen concentration of 7.5 mole percent or less.

3. A process according to claim 1 wherein (1) said measuring of the oxygen concentration of said gaseous effluent is after gas and liquid separation of the cooled effluent and (2) said recycled $C_4$ hydrocarbon-containing stream is introduced into said cooled effluent prior to gas and liquid separation.

4. A process according to claim 1 wherein said stream is a recycled butadiene concentrate comprising butadiene, butenes, and butane separated from the effluent of a butenes oxidative dehydrogenation process.

5. A process for maintaining the oxygen concentration below the combustible limit in the effluent from the oxidative dehydrogenation of olefins which comprises:
   a. contacting a butenes-containing feed with oxygen-containing gas in the presence of an oxidative dehydrogenation catalyst at oxidative dehydrogenation conditions to form an effluent comprising butadiene, unconverted butenes, oxygen, nitrogen, steam, and oxygenated hydrocarbon impurities,
   b. cooling said effluent sufficiently to condense steam and form a water condensate,
   c. separating said condensate from said effluent leaving a gaseous stream comprising butadiene, butenes, oxygen, nitrogen, and some oxygenated hydrocarbon, and other impurities,
   d. measuring the oxygen concentration of said gaseous stream in (c) and producing a signal representative thereof,
   e. subjecting said stream in (c) to additional separation whereby a butadiene concentrate stream comprising butadiene and butenes is recovered, and
   f. controlling the oxygen concentration of said effluent responsive to said signal by recycling at least a portion of said butadiene concentrate to said effluent after said cooling (b) but prior to said separating (c) in an amount sufficient to regulate and maintain the residual oxygen concentration in said effluent to a safe value below 9.5 mole percent.

6. A process according to claim 5 wherein said measuring of step (d) is carried out by analyzing the oxygen concentration of the gas phase of the separation zone in step (c) and a signal responsive to this analysis is compared with a desired set point value of oxygen concentration and a second signal is generated which is representative of the difference and which signal is used to control the rate of introduction of said concentrate into said effluent to maintain the oxygen concentration below said safe value.

7. A process according to claim 6 wherein the residual oxygen concentration in said effluent is maintained below about 7.5 mole percent.

* * * * *